United States Patent [19]

Miller

[11] Patent Number: 5,119,828

[45] Date of Patent: * Jun. 9, 1992

[54] SEBUM INDICATOR WITH LIGHT ABSORBING VISUALIZATION ENHANCER

[75] Inventor: David L. Miller, Dallas, Tex.

[73] Assignee: CuDerm Corporation, Dallas, Tex.

[*] Notice: The portion of the term of this patent subsequent to Feb. 18, 2009 has been disclaimed.

[21] Appl. No.: 626,482

[22] Filed: Dec. 12, 1990

[51] Int. Cl.$^5$ .................................................. A61B 5/00
[52] U.S. Cl. .................................................. 128/760
[58] Field of Search ............... 128/760, 759, 632, 630, 128/749, 771, DIG. 18, 156; 604/317, 318, 327, 289, 290, 304, 307, 312; 436/71; 422/55, 82.05, 82.09; 350/534, 266

[56] References Cited

U.S. PATENT DOCUMENTS

| | | |
|---|---|---|
| 3,906,933 | 9/1975 | Tur et al. .................. 128/759 |
| 4,190,060 | 2/1980 | Greenleaf et al. .................. 128/760 |
| 4,224,950 | 9/1930 | Bore et al. .................. 128/759 |
| 4,532,937 | 8/1985 | Miller .................. 128/759 |
| 4,981,145 | 1/1991 | Goldstein .................. 604/312 |

Primary Examiner—Max Hindenburg
Assistant Examiner—Guy V. Tucker
Attorney, Agent, or Firm—Ross, Howison, Clapp & Korn

[57] ABSTRACT

A device for collecting sebum which is secreted from the sebaceous glands of a subject includes a microporous, hydrophobic polymeric film which is opaque to light when the pores are filled with gaseous material and which is substantially translucent when the film pores are filled with sebum. The film is mounted to a substrate which includes a light absorbing area for enhancing visualization of the film pores when filled with sebum.

2 Claims, 1 Drawing Sheet

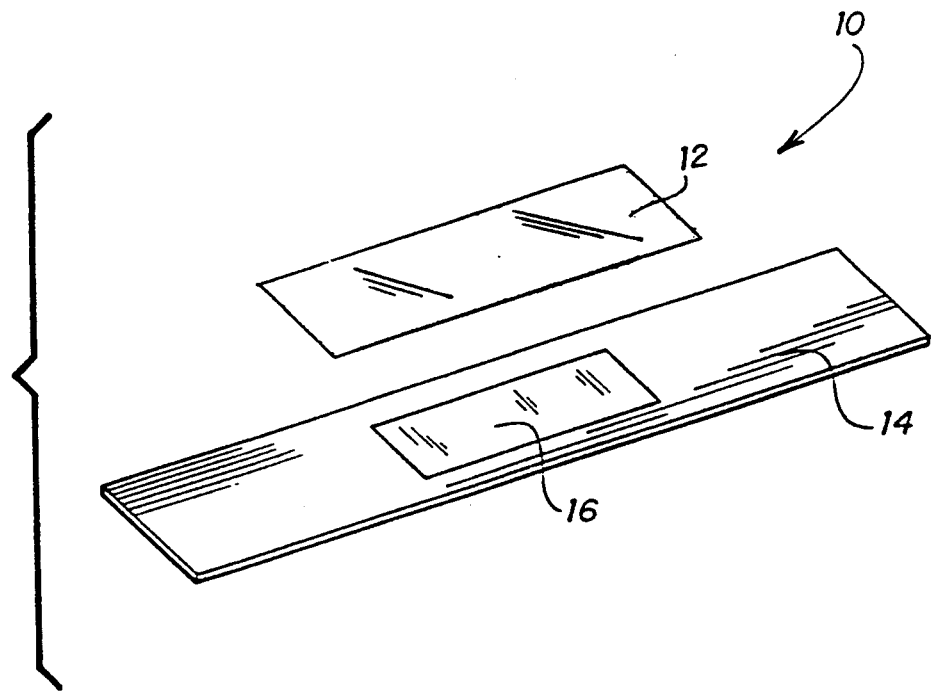

SEBUM INDICATOR WITH LIGHT ABSORBING VISUALIZATION ENHANCER

TECHNICAL FIELD OF THE INVENTION

This invention relates to skin surface sampling devices, and more particularly to a device for collecting sebum.

BACKGROUND OF THE INVENTION

The sebaceous glands, located under the skin near hair follicles, secrete a greasy or oily substance known as sebum. Sebum normally flows through the sebaceous duct and into the hair follicle and from there to the surface of the skin, where it is useful to lubricate the skin and hair. The largest sebaceous glands in humans are those which secrete sebum at the greatest rate and are located on the face, scalp and back. When the sebaceous glands operate to secrete the desired amount of sebum, the skin appears fresh and alive. When too little sebum flows, the skin becomes dry and tends to crack and wrinkle. When excessive sebum is secreted, a characteristic greasy appearance of the skin is observed. Excessively oily skin is a problem associated with adolescents and can result in acne, in which the duct of the follicle canal is hyperkeratinized, leading to the creation of sacks plugged with liquids and solids. In addition, the undesirable nature of oily films on the skin has an adverse effect on the appearance of women's cosmetics and makeup, often causing them to change color or shade.

Several methods have been proposed to collect and quantify the secretions from sebaceous glands. One such method and device is disclosed in U.S. Pat. No. 4,532,937 in which a microporous film is adhesively attached to the skin for absorbing sebum. After removal from the skin, the film contains surface patterns that can be compared to standards for determining the location and relative rate of secretion of sebaceous glands on the subject's skin. A device for observing the degree of dry skin is disclosed in U.S. Pat. No. 5,088,502.

A need has arisen for an improved device for collecting sebum to provide a highly visible indication of sebum absorption by a monitoring device.

SUMMARY OF THE INVENTION

In accordance with the present invention, a device for collecting sebum which is secreted from the sebaceous glands of a subject is provided. The device includes a microporous, hydrophobic polymeric film which is opaque to light when the pores are filled with gaseous material and which is substantially translucent when the film pores are filled with sebum. The film is mounted to a substrate which includes a light absorbing area for enhancing visualization of the film pores when filled with sebum.

BRIEF DESCRIPTION OF THE DRAWING

For a more complete understanding of the present invention and for further advantages thereof, reference is now made to the following Description of the Preferred Embodiments taken in conjunction with the accompanying Drawing which is an exploded perspective view of the present invention.

DESCRIPTION OF THE PREFERRED EMBODIMENTS

Referring to the FIGURE, the present sebum collecting device is illustrated, and is generally identified by the numeral 10. Sebum collecting device 10 includes a microporous, hydrophobic polymeric film 12. Film 12 is generally described in U.S. Pat. No. 4,532,937, which description is hereby incorporated by reference.

Film 12 is mounted to a substrate 14 such as, for example, a stiff paper board material. Disposed on substrate 14 is an area 16 having light absorbing characteristics such as, for example, a darkened colored area which is printed on substrate 14 using standard printing techniques. Film 12 is mounted to substrate 14 by gluing, heat sealing or other affixation techniques in the area immediately adjacent to area 16 such that film 12 does not adhere to area 16.

Sebum collecting device 10 is utilized to collect sebum by pressing device 10 firmly against the skin surface of a subject with film 12 contacting the skin surface. Film 12 absorbs the sebum present on the skin's surface and the pores of film 12 become substantially translucent when filled with sebum. A sebum spot pattern is thereby developed in film 12 which is visually enhanced through the use of area 16 as a background present on substrate 14. The enhanced visualization is created by the light absorbing area 16 providing a background for the spot pattern created on film 12 through the presence of sebum collected by device 10.

It therefore can be seen that the present invention provides for a sebum collecting device that can be easily used for quick and simple applications to the skin for absorbing sebum as well as for providing an enhanced visual display of a sebum spot pattern for diagnostic purposes.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. A device for sampling and observing the amount of superficial sebum present on the surface of skin of a subject, the device comprising:

a microporous, hydrophobic polymeric film being opaque to light when pores therein are filled with gaseous material and being substantially translucent when said film pores are filled with sebum; and a substrate for mounting said film, said substrate including a dark colored light absorbing area printed on said substrate in the area on which said film is mounted for enhancing visualization of said film pores filled with sebum.

2. The device of claim 1 wherein said film is attached to said substrate in the area surrounding said light absorbing area.

* * * * *